(12) United States Patent
Furnas

(10) Patent No.: US 7,120,284 B2
(45) Date of Patent: Oct. 10, 2006

(54) CONTAINER INSPECTION MACHINE

(75) Inventor: William J. Furnas, Elmira, NY (US)

(73) Assignee: Emhart Glass S.A., Cham (CH)

( * ) Notice: Subject to any disclaimer, the term of this patent is extended or adjusted under 35 U.S.C. 154(b) by 699 days.

(21) Appl. No.: 10/622,766

(22) Filed: Jul. 18, 2003

(65) Prior Publication Data
US 2005/0013473 A1  Jan. 20, 2005

(51) Int. Cl.
*G06K 9/00* (2006.01)
*G01N 21/90* (2006.01)

(52) U.S. Cl. .................... 382/142; 250/223 B
(58) Field of Classification Search ............... 382/142; 250/223 B
See application file for complete search history.

(56) References Cited

U.S. PATENT DOCUMENTS 5,496,996 A * 3/1996 Barnes et al. ........... 250/223 B
5,536,935 A * 7/1996 Klotzsch et al. ........ 250/223 B
6,172,748 B1 * 1/2001 Sones et al. ............. 356/237.1
6,175,107 B1 * 1/2001 Juvinall ................... 250/223 B
6,324,253 B1 * 11/2001 Yuyama et al. ............... 378/57
6,452,156 B1   9/2002 Lindner
6,618,495 B1 * 9/2003 Furnas ....................... 382/142
6,654,116 B1 * 11/2003 Kwirandt ................. 356/240.1
6,859,270 B1 * 2/2005 Werzinger et al. ....... 356/239.1
2001/0054680 A1* 12/2001 Lindner ................... 250/223 B
2003/0035103 A1* 2/2003 Werzinger et al. ....... 356/239.1

FOREIGN PATENT DOCUMENTS

EP 0280933 9/1988
JP 2002-052187 * 2/2002

* cited by examiner

*Primary Examiner*—Jingge Wu
*Assistant Examiner*—Brian Le
(74) *Attorney, Agent, or Firm*—Spencer T. Smith

(57) ABSTRACT

An L.E.D. matrix light source illuminates a bottle at an inspection machine. A vertically periodic intensity pattern is defined to facilitate the identification of defects. The L.E.D. that locates the top of the bottle is identified and a peak of the pattern is located at that L.E.D.

2 Claims, 3 Drawing Sheets

CONTAINER INSPECTION MACHINE

The present invention relates to machines which have a camera based inspection system for inspecting bottles for defects.

BACKGROUND OF THE INVENTION

Machines for inspecting glass bottles conduct a great variety of inspections. More and more of these inspections are conducted using camera technology and often the light source is made up of a L.E.D. matrix. Conventionally the intensity of a vertical row is varied relative to the intensity of neighboring rows to achieve sinusoidal or triangular intensity patterns which facilitate the identification of defects.

OBJECT OF THE INVENTION

It is an object of the present invention to provide a system for inspecting glass containers using such a L.E.D. matrix and to be able to define bottle height with the matrix.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE PREFERRED EMBODIMENT

Figure 1:
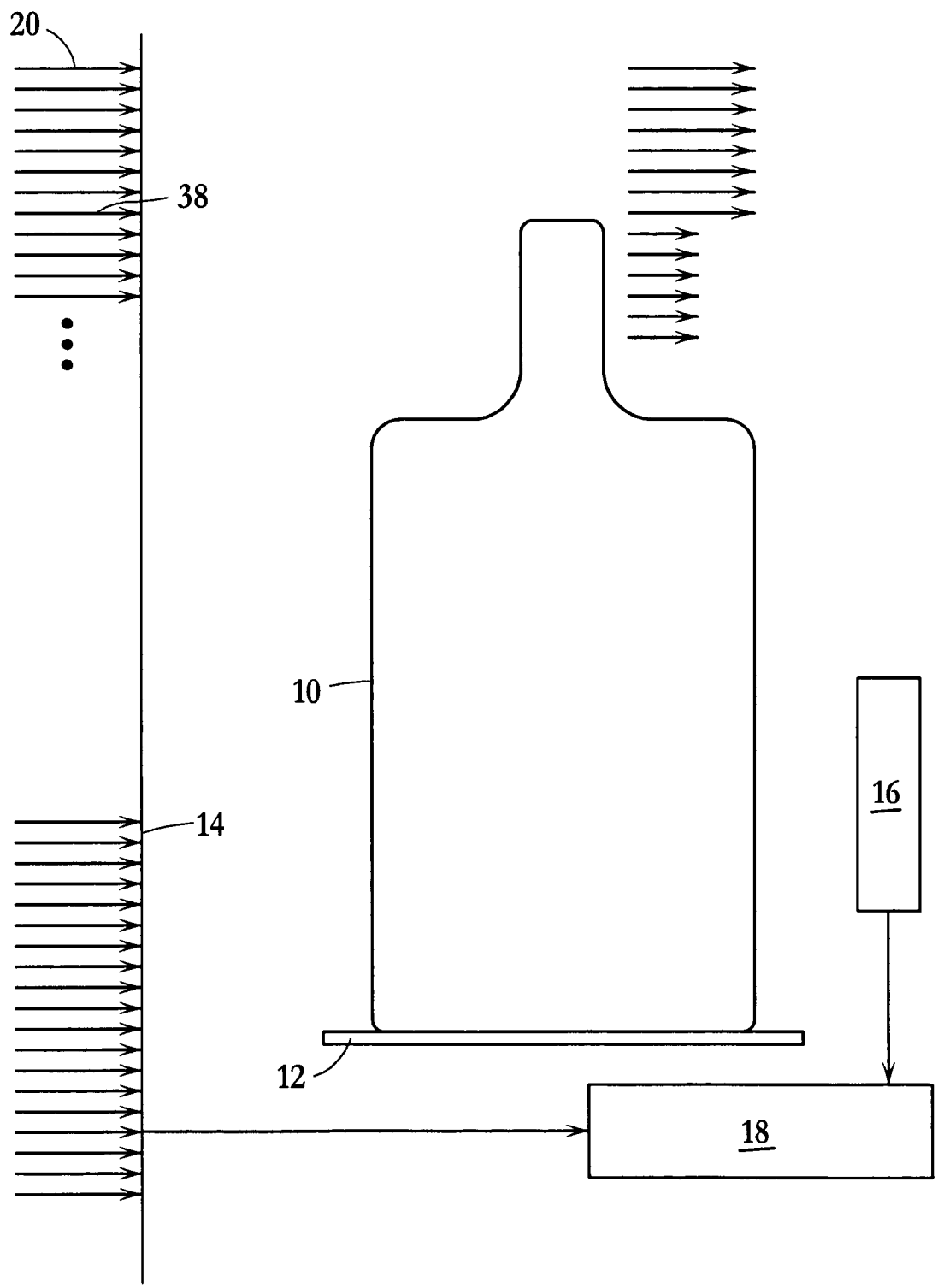
FIG. 1 is a schematic illustration showing a bottle supported by a conveyor at an inspection station where it is illuminated by a light matrix and the image is evaluated by a camera system.

FIG. 1 shows a bottle 10 supported by a conveyor 12 at an inspection station. A light source 14 in the form of a rectangular or square L.E.D. matrix directs light horizontally through the bottle and the bottle is imaged on a suitable camera 16 and this image is evaluated by a processor 18. The light source is schematically represented by a single vertical row of L.E.D.'s, whereas there would in fact be numerous vertical rows. In FIG. 1, the intensity of all the L.E.D's is the same as represented by equal length intensity arrows 20. The intensity of each L.E.D. defining the light source 14 is controlled by the processor.

To the right of the top of the bottle in FIG. 1 are intensity arrows which are representative of the intensity of light imaged on the camera in this area. Above the top of the bottle the light intensity would be equal to the intensity of the light emitted from the light source and down from the top of the bottle, as shown by the shorter intensity arrows light transmitted to the camera would be of a much lower intensity.

Figure 2:
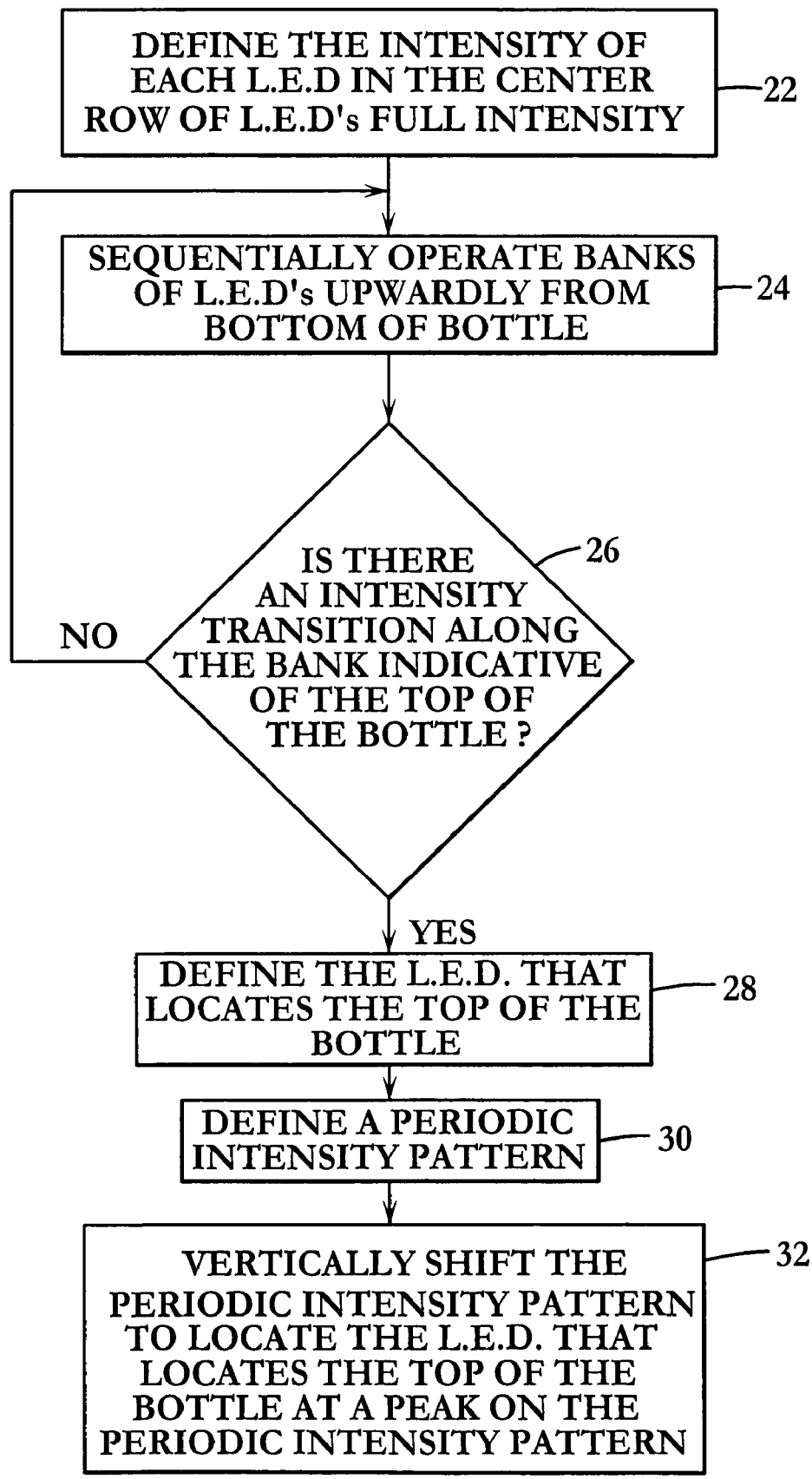
FIG. 2 is a schematic diagram for a temperature correction circuit for the voltage applied in FIG. 1.

The control algorithm is shown in FIG. 2. The processor first proceeds, during a setup mode, to Define The Intensity Of Each L.E.D. In The Center Row Of L.E.D.'s Full Intensity 22 (the processor would know which vertical row was the central row since the location of the bottle at the inspection station is located directly or indirectly via a sensor and the center row could be one or more vertical rows). To determine the height of the bottle, the processor would then Sequentially Operate Banks of L.E.D.'s Upwardly From The Bottom Of The Bottle 24 (a bank might, for example, be four vertically spaced L.E.D.'s). In this illustration, the lowest bank would be operated at full intensity, then the bank vertically above, etc. The intensity gradient of the imaged light of each bank is evaluated. When the operated bank intersects the top of the bottle the processor will answer the inquiry "Is There An Intensity Transition Along The Bank Indicative Of The Top Of The Bottle?" 26 in the affirmative and will then Define The L.E.D. That Locates The Top Of The Bottle 28. For purposes of illustration, the arrow representing light from the L.E.D. that locates the top of the bottle is indexed 38.

Figure 3:
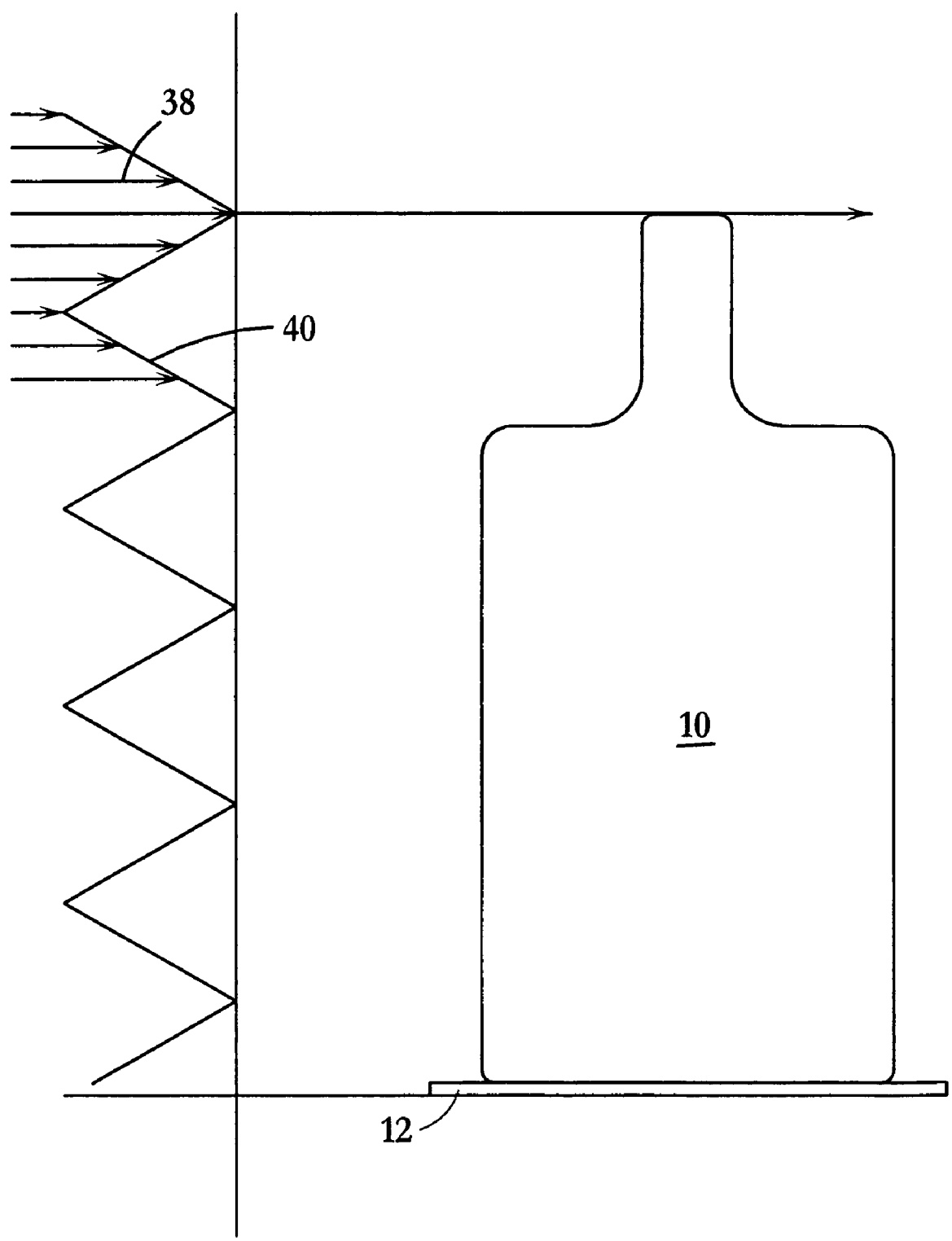
FIG. 3 is view similar to that of FIG. 1 showing a triangulated periodic intensity pattern.

To inspect a bottle a periodically varying light intensity is defined. The intensity of each L.E.D. in a horizontal row will be uniform but the intensity of the horizontal rows will vary. Varying intensity per a sinusoidal curve which in the ideal is a triangulated form enables the identification of defects in the sidewall of the bottle. FIG. 3 illustrates a periodically repeating triangulated intensity gradient 40 for a vertical row of L.E.D.s. The vertical period from one peak to the next peak (or from one low to the next low) corresponds to a selected number of horizontally extending L.E.D. rows (14 for example). In the disclosed embodiment the intensity varies between full intensity and a low intensity every 14 L.E.D.'s but it could also vary between full intensity and black. It should be noted that to achieve the triangulated intensity pattern shown, the intensity of individual rows of L.E.D.'s will have to be adjusted and these L.E.D. settings will be stored in memory so that the processor can establish this triangulated intensity pattern.

Referring again to FIG. 2, the processor then proceeds to Define A Periodic Intensity Pattern 30 and then to Vertically Shift The Periodic Intensity Pattern To Locate The L.E.D. That Locates The Top Of The Bottle At A Peak On The Periodic Intensity Pattern 32 (arrow 38 represents light from the L.E.D. that locates the top of the bottle).

The invention claimed is:

1. A machine for inspecting a bottle comprising
    a conveyor for supporting a bottle at an inspection location, and
    an inspection system for inspecting a bottle at the inspection location including
        a camera having an imaging surface on one side of the bottle,
        an L.E.D. matrix light source having a plurality of horizontal L.E.D. rows on the other side of the bottle directing light towards said camera, and
        a processor
            for defining a vertical periodic intensity pattern having intensity peaks and valleys, for a vertical row of L.E.D.s and
            for locating the L.E.D of the vertical row that locates the top of a bottle to be inspected at a peak of the periodic intensity pattern.

2. A machine for inspecting a bottle according to claim 1, wherein the periodic intensity pattern is a triangulated pattern.

* * * * *